United States Patent

Lecouve

Patent Number: 5,426,243
Date of Patent: Jun. 20, 1995

[54] PROCESS FOR PREPARING 1,6-DIBROMO-2-NAPHTHYLENE COMPOUNDS

[75] Inventor: Jean-Pierre Lecouve, Mulhouse, France

[73] Assignee: Albemarle Corporation, Richmond, Va.

[21] Appl. No.: 291,805

[22] Filed: Aug. 17, 1994

[51] Int. Cl.$^6$ .................. C07C 39/38; C07C 39/24
[52] U.S. Cl. .................. 568/737; 568/735; 568/779
[58] Field of Search .................. 568/737, 779

[56] References Cited

U.S. PATENT DOCUMENTS

| | | | |
|---|---|---|---|
| 4,628,123 | 12/1986 | Borsotti | 568/634 |
| 4,855,514 | 8/1989 | Rule et al. | 568/779 |
| 4,876,396 | 10/1989 | LeBlance et al. | 568/779 |
| 4,885,408 | 12/1989 | Ratton et al. | 568/779 |
| 5,243,088 | 9/1993 | Jacquot | 568/656 |
| 5,256,829 | 10/1993 | Jacquot | 568/737 |

FOREIGN PATENT DOCUMENTS 748621  4/1944  Germany .

Primary Examiner—Werren B. Lone
Attorney, Agent, or Firm—Philip M. Pippenger

[57] ABSTRACT

An improved process for the preparation of 1,6-dibromo-2-naphthol is disclosed. The improvement is accomplished by carrying out the reaction in an organic solvent at a temperature of from about 40° to about 60° C. in the presence of a catalytically-effective amount of a compound of the formula:

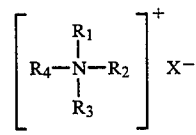

where $R_1$, $R_2$, $R_3$ and $R_4$ are the same or different and are alkyl, cycloalkyl, phenyl, substituted phenyl, naphthyl, substituted naphthyl heteroaryl, substituted heteroaryl or $R_1$ taken together with $R_2$ and the nitrogen atom form a heteroaryl or substituted heteroaryl group in which the heteroatom is nitrogen and X is an inorganic anion.

5 Claims, No Drawings

PROCESS FOR PREPARING 1,6-DIBROMO-2-NAPHTHYLENE COMPOUNDS

FIELD OF THE INVENTION

This invention relates to an improved method for preparing 1,6-dibromo-2-naphthylene compounds prepared by bromination of β-naphthol.

BACKGROUND OF THE INVENTION 1,6-dibromo-2-hydroxynaphthalene is an intermediate used in the preparation of certain pharmaceutically-active compounds. For example, according to EP-A-179,447, 6-bromo-2-naphthalenes may be prepared by stoichiometric metallic reduction of the corresponding 1,6-dibromo-2-naphthalenes by the following reaction:

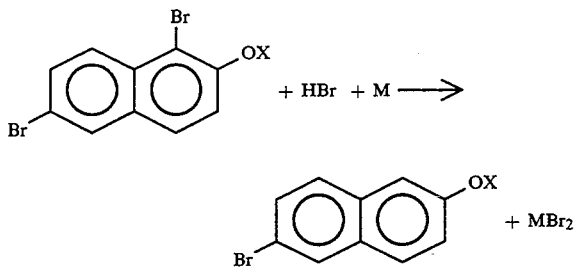

in which X is hydrogen or an alkyl radical, and M is a reducing metal such as iron or tin.

The 6-bromonaphthalenes above are known and valuable compounds. For example, 6-bromo-2-methoxynaphthalene is widely used for synthesizing naproxen or nabumetone, two pharmaceuticals which are well known for their therapeutic anti-inflammatory properties and also for synthesizing methallenestril, which is an estrogen [compare *The Merck Index*, eleventh edition, pages 1002, 1014 and 937 (1989)].

The above dibrominated compounds may themselves be simply prepared by direct bromination of the corresponding nonbrominated compounds:

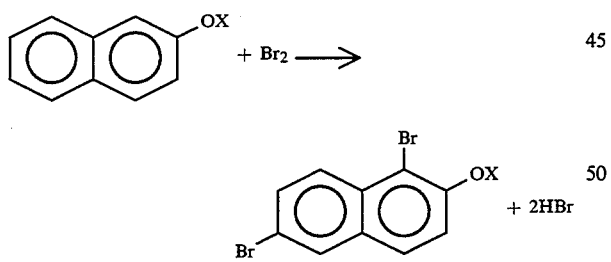

However, reducing dibrominated derivatives of naphthalene to monobrominated derivatives by a method as described above presents the disadvantage, inter alia, of requiring large amounts of metal, which metal is ultimately present in the reaction effluent which is difficult to salvage and often becomes a pollutant, such as FeBr$_2$.

Moreover, the yield of the desired monobrominated compounds from such a process may prove to be inadequate.

U.S. Pat. No. 5,243,088 teaches a method for treating the 1,6-dibromo compounds with nascent hydrogen and a catalyst to yield the 1-mono-dibrominated product. Also see U.S. Pat. No. 5,256,829 and U.S. Pat. No. 4,628,123. These processes disadvantageously produce copious amounts of high molecular weight by-products. Further, the selective determination is difficult to control, with by-product 2-naphthol formation diminishing yields of the desired bromo-compound.

There remains a need for carrying out the preparation of 1,6-dibromo-2-hydroxynaphthylinic compounds with high regriselectivity and minimum formation of high molecular weight by-products.

SUMMARY OF THE INVENTION

In summary, the present invention relates to a process for preparing 1,6-dibromo-2-naphthylinic compounds by the treatment of β-naphthol with elemental bromine.

The above process has been improved by carrying the reaction out in an organic solvent at an elevated temperature of from about 40° to about 60° C. in the presence of a compound of the formula:

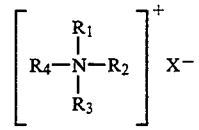

where R$_1$, R$_2$, R$_3$ and R$_4$ are the same or different and are alkyl, cycloalkyl, phenyl, substituted phenyl, naphthyl, substituted naphthyl, heteroaryl, substituted heteroaryl or R$_1$ taken together with R$_2$ and the nitrogen atom from a heteroaryl as substituted heteroaryl group in which the heteroatom is nitrogen and X is an inorganic anion.

DESCRIPTION OF THE PREFERRED EMBODIMENTS

In the present specification, "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

"cycloalkyl" means cyclic alkyl having 3 to 7 carbon atoms and includes cyclopropyl, cyclobutyl, cyclopentyl, cyclo-hexyl and cycloheptyl;

"substituted phenyl" or "substituted naphthyl" means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloro-propyl, 3-bromopropyl, 3-fluoropropyl, 4-chlorobutyl, 4-fluoro-butyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

"heteroaryl" means 5 to 10 membered mono- or fused-heteroaromatic ring which as at least one heteroatoms selected from the group consisting of nitrogen, oxygen and sulfur and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl; and "substituted heteroaryl" means to 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the abovementioned heteroaromatic nucleus.

As noted above, the process of the present invention employs as a catalyst certain compounds that had heretofore been known as useful for fabric softeners, antistatis agents organomodified clays, etc. These catalysts have the formula:

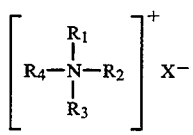

wherein $R_1$, $R_2$, $R_3$ and $R_4$ are the same or different and are alkyl, cycloalkyl, phenyl, substituted phenyl, naphthyl, substituted naphthyl, heteroaryl, substituted heteroaryl as $R_1$ taken together with $R_2$ and the nitrogen atom form a heteroaryl or substituted heteroaryl group in which the heteroatom is nitrogen and X is an inorganic anion, usually halide, sulfate, phosphate, etc.

The preferred quaternary ammonium salts are those where X is halo and $R_1$, $R_2$ $R_3$ and $R_4$ are the same or different and are alkyl, phenyl or substituted phenyl. Most preferred are the salts where $R_1$, $R_2$, $R_3$ and $R_4$ are the same or different and are alkyl.

Particularly preferred ammonium salts are:
trimethylcetylammonium chloride;
trimethylcetylammonium bromide;
trimethyldodecylammonium chloride;
trimethyldodecylammonium bromide;
trimethyloctadecylammonium chloride;
trimethyloctadecylammonium bromide;
trimethylhexadecylammonium chloride;
trimethylhexadecylammonium bromide;
dimethylalkylbenzylammonium chloride; where the alkyl groups are as follows: n-$C_{12}H_{25}$; n-$C_{14}H_{29}$; n-$C_{16}H_{33}$; n-$C_{18}H_{37}$;
methylbis(2-hydroxyethyl)octadecylammonium chloride;
methylpolyoxyethylene (15) octadecylammonium chloride;
n-dodecyl (61%) tetradecyl (23%) dimethylbenzylammonium chloride;
n-tetradecyl (60%) hexadecyl (30%) dimethylbenzylammonium chloride;
n-dodecyl (40%) tetradecyl (50%) dimethylbenzylammonium chloride;
n-dodecyl (61%) tetradecyl (23%) dimethylbenzylammonium chloride;
n-octadecyldimethylbenzylammonium chloride;
42% n-tetradecyl (40%) hexadecyl (60%) dimethylbenzylammonium chloride;
8% dialkylmethylbenzylammonium chloride;
n-dodecyl (35%) tetradecyl (5%) hexadecyl (60%) dimethylbenzylammonium chloride;
n-dodecyl (20%) tetradecyl (50%) hexadecyl (30%) dimethylbenzylammoniumbromide;
methyl sulfate quaternary of ethoxylated tallow diethylenetriamine condensate;
methyl sulfate quaternary of propoxylated tallow diethylenetriamine condensate; and
1-(tallow amidoethylene)-2-nor (tallow alkyl)-2-imidazolinium, methyl sulfate quaternary.

Methods of preparation for the quaternary ammonium compounds useful in carrying out the process of the present invention are numerous and vary depending on the structure of the final compound. Typical reactions are, for example, where a suitable tertiary amine reacts with an alkylating agent, which can be an alkyl ester. The reactions are summarized in Kirk-Other, *Encyclopedia of Chemical Technology*, Third Edition, Volume 19, incorporated herein by references.

The preparation of 1,6-dibromo-2-naphthol is conveniently carried out by first admixing β-naphthol in an organic solvent. Such organic solvents include the halogenated solvents, e.g., perchloroethylene, dichloroethane, etc., cycloaliphatic solvents, e.g., cyclohexane, methylcyclohexane, etc., aliphatic solvents, e.g., heptane, octane, etc. or the aromatic solvents, e.g., benzene toluene, etc.

It should be noted that the catalysts of use in this improved process have typically found use elsewhere in aqueous media. The organic solvent assures that the debrominated product readily precipitates. It can be separated as set forth herein.

To the solution of β-naphthol, an organic solvent is added to one or more of the catalysts of the present invention. The resulting solution is heated to at least about 40° C. and up to above 60° C. for the successful addition of bromine to the naphthalene nucleus. Elemental bromine is added over a period of from about two hours to about four hours. At lower temperatures, very little dibromination occurs within any meaningful time. Higher temperatures produce undesirable amounts of high molecular weight by-products.

As noted, a catalytically-effective amount of the catalyst is all that is necessary to enhance the reaction of bromine with β-naphthol. Typical amounts of catalyst (based on β-naphthol) are from about 0.01 mole per mole of β-naphthol to about 0.10 mole per mole.

After the reaction is complete, the product is separated from the reaction mass by conventional methods, e.g., extraction and recrystallization, vacuum distillation, etc.

The following examples are for the purposes of illustration. They are not meant to limit the invention in any manner.

| Analysis of Reaction Mixtures and Mother Liquors | | | | | |
|---|---|---|---|---|---|
| (1) Reaction Mixture After Post Reaction | | | | | |
| Trial | "X" Unidentified Compound | Bromo-1-naphthol | 1,6-DBN | Polybrominated Compound | Heavy Compound | % $BR_2$ |
| 201 | 1.08 | 0.6 | 03.3 | 1.3 | 1.0 | 106 |
| 202 | 2.75 | 0.4 | 91.9 | 1.5 | 1.3 | 106 |
| 203 | 3.8 | 0.4 | 89.2 | 1.9 | 1.2 | 106 |

-continued

| Analysis of Reaction Mixtures and Mother Liquors | | | | | |
|---|---|---|---|---|---|
| 204 | 3.9 | 4.2 | 87.2 | 1.5 | 1.5 | 103 |
| 205 | 5.1 | 1.8 | 87.0 | 1.5 | 1.6 | 106 |
| 206 | 7.1 | 1.6 | 82.2 | 1.5 | 1.5 | 106 |

| (2) Analysis of Mother Liquors | | | | | |
|---|---|---|---|---|---|
| Trial | "X" Unidentified Compound | Bromo-1-napthol | 1,6-DBN | Poly brominated Compound | % of Solid in Mother Liquors |
| 201 | 8.4 | 1.5 | 66.5 | 9.4 | 2.1 |
| 202 | 16.2 | 2.3 | 52.6 | 3.4 | 4.1 |
| 203 | 19.6 | 2.8 | 51.4 | 9.9 | 5.0 |
| 204 | 18.8 | 14.4 | 38.9 | 4.0 | 6.2 |
| 205 | 18.2 | 10.5 | 39.5 | 4.5 | 6.3 |
| 206 | 19.0 | 11.8 | 42.0 | 4.5 | 7.3 |

1,6-DIBROMONAPHTHOL (1,6-DBN)
Summary of 5 Recycling Synthesis in Methylcyclohexane

| Trial | % Br$_2$ | % Br$_2$ feed at 50° C. | Br$_2$ Feed Time at 50° C. | % Br$_2$ Feed at 70° C. | Br$_2$ Feed Time at 70° C. | Time for post Reaction mm | Br? Naphthol % | Br$_6$ Naphthol % | X % | DBN % |
|---|---|---|---|---|---|---|---|---|---|---|
| 201 | 106 | 100 | 40' | 0 | — | 120 | 0.21 | 0.81 | 0.8 | 96.87 |
| 202 | 106 | 80 | 30' | 20 | 45' | 120 | 0.12 | 0.72 | 0.35 | 93.67 |
| 203 | 106 | 93 | 35' | 7 | 10' | 120 | 0.27 | 0.74 | 1.15 | 96.05 |
| 204 | 103 | 80 | 28' | 20 | 18' | 120 | 0.77 | 0.65 | 1.38 | 94.9 |
| 205 | 106 | 80 | 30' | 20 | 45' | 120 | 0.47 | 0.58 | 1.48 | 95.3 |
| 206 | 106 | 80 | 30' | 20 | 45' | 120 | 0.46 | 0.79 | 1.46 | 93.7 |

| Trial | Poly-bromine % | Heavy % | Yield % | Fusion Point °C. | Color Alpha | Br % | Volatiles % | K.F. | Cumulated Yield % |
|---|---|---|---|---|---|---|---|---|---|
| 201 | 0.41 | 0.80 | 91.09 | 106.6 | 160 Filter | 0.56 | 0.14 | <0.05 | 91.09 |
| 202 | 0.74 | 4.00 | 95.33 | 106.4 | 65 Filter | 0.28 | 0.25 | 0.020 | 93.2 |
| 203 | 0.65 | 0.23 | 100.99 | 105.9 | 98 Filter | 0.64 | 0.23 | 0.025 | 95.8 |
| 204 | 0.8 | — | 93.31 | 105.3 | 70 Filter | 0.22 | 0.17 | 0.10 | 95.17 |
| 205 | 1.1 | 0.25 | 96.34 | 106.7 | 70 Filter | 0.21 | 0.27 | 0.06 | 95.4 |
| 206 | 1.81 | 0.46 | 97.24 | 105.1 | 75 Filter | 0.26 | 0.16 | 0.060 | 95.7 |

The above examples clearly demonstrate the improved process of the present invention provide good regioselectivity (the formation of high molecular weight by-products and 2-naphthol is greatly reduced); and the debrominated naphthol precipitates readily from the reaction solution and is easily removed by, for example, filtration.

I claim:

1. In a process for the preparation of 1,6-dibromo-2-naphthol wherein β-naphthol is dissolved in an organic solvent and brominated with elemental bromine, the improvement comprising carrying out the process at a temperature of from about 40° to about 60° C. in the presence of a catalytically-effective amount of a compound of the formula:

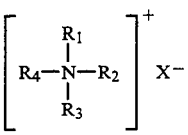

where $R_1$, $R_2$, $R_3$ and $R_4$ are the same or different and are alkyl, cycloalkyl, phenyl, substituted phenyl, naphthyl, substituted naphthyl heteroaryl, substituted heteroaryl or $R_1$ taken together with $R_2$ and the nitrogen atom form a heteroaryl or substituted heteroaryl group in which the heteroatom is nitrogen and X is an inorganic anion.

2. The process of claim 1 wherein X is a halide anion.

3. The process of claim 2 wherein $R_1$, $R_2$, $R_3$ and $R_4$ are the same or different and are alkyl, phenyl or substituted phenyl.

4. The process of claim 3 wherein $R_1$, $R_2$, $R_3$ and $R_4$ are the same or different and are alkyl.

5. The process of claim 4 wherein $R_1$, $R_2$, $R_3$ and $R_4$ is cetyl.

* * * * *